(12) United States Patent
Aoki et al.

(10) Patent No.: US 8,920,749 B2
(45) Date of Patent: Dec. 30, 2014

(54) MICROCHIP AND LIQUID SENDING METHOD FOR MICROCHIP

(71) Applicant: Konica Minolta, Inc., Tokyo (JP)

(72) Inventors: Youichi Aoki, Hachioji (JP); Akihisa Nakajima, Tama (JP); Kusunoki Higashino, Osaka (JP); Yasuhiro Sando, Amagasaki (JP); Yoshikazu Kurihara, Uenohara (JP)

(73) Assignee: Konica Minolta Medical & Graphic, Inc. (JP)

( * ) Notice: Subject to any disclaimer, the term of this patent is extended or adjusted under 35 U.S.C. 154(b) by 0 days.

(21) Appl. No.: 13/966,933

(22) Filed: Aug. 14, 2013

(65) Prior Publication Data

US 2014/0162373 A1 Jun. 12, 2014

Related U.S. Application Data

(62) Division of application No. 12/809,137, filed as application No. PCT/JP2008/072310 on Dec. 9, 2008, now abandoned.

(30) Foreign Application Priority Data

Dec. 21, 2007 (JP) .................... 2007-329850

(51) Int. Cl.
  *B01L 3/00* (2006.01)
  *G01N 21/03* (2006.01)
  *G01N 35/00* (2006.01)

(52) U.S. Cl.
  CPC ......... *B01L 3/502746* (2013.01); *B01L 3/5027* (2013.01);
  (Continued)

(58) Field of Classification Search
  CPC ............ C12Q 2565/629; G01N 2021/0346; B01L 9/527; B01L 2200/0673; B01L 2300/165; B01L 3/5027; B01J 2219/00619
  USPC .............. 422/52, 82.05, 82.06, 82.07, 82.08, 422/82.09, 82.11, 407, 501, 502, 503; 435/164, 165, 283.1, 287.1, 287.2, 435/288.7, 808, 4, 5, 7.2, 7.9; 436/164, 436/165, 172, 174, 518, 805, 809; 204/403.01; 506/3, 39; 359/321; 250/458.1, 559.29, 574; 356/128, 244, 356/246, 300, 326, 414, 416, 445; 430/290, 430/321

See application file for complete search history.

(56) References Cited

U.S. PATENT DOCUMENTS

2007/0047388 A1 3/2007 DeNatale et al.
2008/0280365 A1 11/2008 Grumann et al.

FOREIGN PATENT DOCUMENTS

DE   10325110 B3   1/2005
DE   102005048236 A1   4/2007
(Continued)

OTHER PUBLICATIONS

Extended European Search Report for Application No./Patent No. 08864694.8-1361/2224249, dated Sep. 30, 2013.
(Continued)

*Primary Examiner* — Dennis M White
(74) *Attorney, Agent, or Firm* — Cantor Colburn LLP (57) ABSTRACT

A microchip capable of sending liquid in a micro flow channel to a predetermined place irrespective of the pressure difference and sending a mixture of two or more liquid masses to a predetermined place even if the channel structure is simple. The microchip comprises an intermediate reservoir portion provided in a micro flow channel and adapted for temporarily holding liquid sent through the micro flow channel. The microchip is characterized in that the intermediate reservoir portion has a side channel, the volume of the intermediate reservoir portion is smaller than the total volume of the liquid sent into the intermediate reservoir portion, the side channel is provided for communication of a micro flow channel on the upstream side of the intermediate reservoir portion with a micro flow channel on the downstream side thereof, and the cross-section area of the side channel is smaller than that of the micro flow channel.

8 Claims, 5 Drawing Sheets

(52) U.S. Cl.
CPC ... *B01J 2219/00619* (2013.01); *C12Q 2565/629* (2013.01); *G01N 2021/0346* (2013.01); B01L 3/502723 (2013.01); *B01L 2200/027* (2013.01); *B01L 2200/0642* (2013.01); *B01L 2200/0673* (2013.01); *B01L 2200/16* (2013.01); *B01L 2300/0816* (2013.01); *B01L 2300/0867* (2013.01); *B01L 2400/0487* (2013.01); *G01N 2035/00158* (2013.01); *Y10S 435/808* (2013.01); *Y10S 436/805* (2013.01); *Y10S 436/809* (2013.01)
USPC ....... 422/501; 422/52; 422/82.05; 422/82.06; 422/82.07; 422/82.08; 422/82.09; 422/82.11; 422/407; 422/502; 422/503; 435/164; 435/165; 435/283.1; 435/287.1; 435/287.2; 435/288.7; 435/808; 435/4; 435/5; 435/7.2; 435/7.9; 436/164; 436/165; 436/172; 436/174; 436/518; 436/805; 436/809

(56) References Cited

FOREIGN PATENT DOCUMENTS

| | | |
|---|---|---|
| EP | 1941941 A1 | 7/2008 |
| JP | 2000-27813 A | 1/2000 |
| JP | 2002-236131 A | 8/2002 |
| JP | 2003-279569 A | 10/2003 |
| JP | 2004-28589 A | 1/2004 |
| JP | 2004-226412 A | 8/2004 |
| JP | 2005-169386 A | 11/2004 |
| JP | 2005169386 A | 6/2005 |
| JP | 2006-142242 A | 6/2006 |
| WO | 2007049559 A1 | 5/2007 |

OTHER PUBLICATIONS

Chung et al. "Microfluidic chip accomplishing self-fluid replacement using only capillary force and its bioanalytical application" Analytica Chimica Acta 585 (2007) 1-10.

International Search Report for PCT/JP2008/072310 mailed Feb. 10, 2009 with English translation.

Written Opinion of the International Searching Authority for International Application No. PCT/JP2008/072310 mailed Feb. 10, 2009 with English translation.

FIG. 5c  A-A CROSS SECTION

FIG. 6a

FIG. 6b  B-B CROSS SECTION

MICROCHIP AND LIQUID SENDING METHOD FOR MICROCHIP

CROSS REFERENCE TO RELATED APPLICATIONS

The present application is a divisional application of U.S. patent application Ser. No. 12/809,137, filed on Jun. 18, 2010, the entire contents of which are incorporated herein by reference. Application Ser. No. 12/809,137 is the U.S. National stage of application No. PCT/JP2008/072310, filed Dec. 9, 2008. Priority under 35 U.S.C. §119(a) and 35 U.S.C. §365 (b) is claimed from Japanese Application No. JP2007-329850, filed 21 Dec. 2007, the disclosure of which is also incorporated herein by reference.

TECHNICAL FIELD

The present invention relates to a microchip having a micro flow channel to send liquid and a liquid sending method for a microchip.

BACKGROUND

Over recent years, by manipulating a micromachine technology and an ultra-microfabrication technology, a system has been developed in which a device and a member (for example, a pump, a valve, a flow channel, and a sensor) for conventional sample preparation, chemical analysis, and chemical synthesis are miniaturized and integrated on one chip (for example, Patent Document 1). This is also referred to as a μ-TAS (Micro Total Analysis System) which is a method in which a member referred to as a microchip is mixed with a specimen (for example, a DNA-treated extracted solution obtained via treatment and extraction of urine, saliva, or blood of a subject to be tested) and a reagent, followed by detection of the resulting reaction to examine characteristics of the specimen.

A microchip is produced in such a manner that a substrate made of a resin material or glass material is subjected to groove processing using a photo-litho process (a method to produce grooves by etching a pattern image using chemicals) or laser light and then provided with a microscopic follow channel capable of passing a reagent and a specimen and a reservoir to store the reagent. Various patterns thereof have been proposed.

When specimen characteristics are examined using such a microchip, liquid such as a reagent and a specimen stored in the microchip are sent into a flow channel using a micropump, whereby the reagent and the specimen are allowed to react together, followed by being introduced into a detection section for detection. In the detection section, the targeted substance is detected, for example, by an optical detecting method.

When liquid is sent into a flow channel of a microchip, in the case of the presence of air bubbles or other gases in the liquid or therebetween, these gases need to be eliminated in some cases in order to carry out mixing by controlling liquid sending and reaction/detection of the liquid.

In view of these problems, Patent Document 2 discloses a micro amount liquid control mechanism in which two ducts are communication-connected by a narrow pipe whose inner wall surface is formed to be hydrophobic. In the micro amount liquid control mechanism, the narrow pipe is formed to be hydrophobic, whereby such a constitution is realized that entering of liquid is inhibited but gas can easily be passed. And, via the pressure difference between the two duct interiors, in one duct, the liquid is controlled at any appropriate position. By shaping the arrangement of a plurality of narrow pipes, gas present between liquid clusters is eliminated, whereby two liquid clusters are mixed together.

Patent Document 3 discloses a micro liquid control device featuring a narrow gap section with a narrow gap formed to be hydrophobic in the same manner. In such a narrow gap, gas can easily be passed but the flow of liquid is controlled by the flow channel resistance thereof Further, in the micro liquid control device, a flow channel to pass liquid is arranged and narrow gap sections to pass gas are arranged on both sides thereof In this manner, such a constitution is realized that the liquid flowing in the central flow channel cannot enter the narrow gap sections of the both sides by flow channel resistance, whereby the liquid and the gas can stably be passed.

Patent Document 1: Unexamined Japanese Patent Application Publication (hereinafter referred to as JP-A) No. 2004-28589

Patent Document 2: JP-A No. 2000-27813 (page 5, FIG. 4)

Patent Document 3: JP-A No. 2006-142242

DISCLOSURE OF THE INVENTION

Problems to be Solved by the Invention

In the micro amount liquid control mechanism disclosed in Patent Document 2, liquid is prevented from entering by the flow channel resistance of a narrow pipe. This constitution produces such a problem that when the pressure difference between two ducts exceeds the critical pressure difference $\Delta Pc$, liquid in the ducts is passed through the narrow pipe, whereby position control of the liquid cannot be carried out appropriately. Further, noted is the problem that to mix two liquid clusters, a plurality of narrow pipes need to be provided, whereby the flow channel constitution becomes complicated.

Still further, in the micro liquid control device disclosed in Patent Document 3, two liquid clusters can be mixed by eliminating gas therebetween, but from the viewpoint of the constitution, liquid sending of the liquid clusters is carried out by the liquid sending pressure of the liquid from the upstream side. Therefore, in the case of liquid sending via gas between the liquids, no description is made with respect to further sending of a liquid mixture.

In view of the above problems, an object of the present invention is to provide a microchip capable of sending liquid in a micro flow channel to a predetermined position and of carrying out liquid sending to a predetermined position by mixing at least 2 liquid clusters even with a simple flow channel constitution, independently of pressure difference.

Means to Solve the Problems

The above object is achieved by the below-described invention:

(1) A microchip comprising: a micro flow channel; and an intermediate reservoir to temporally store liquid having been sent through the micro flow channel in a flow channel of the micro flow channel, wherein the intermediate reservoir is provided with a side path and wherein a capacity Vs of the intermediate reservoir is smaller than total amount of liquid sent to the intermediate reservoir; the side path communicatively connects a micro flow channel on an upstream side of the intermediate reservoir to a micro flow channel on a downstream side of the intermediate reservoir; and the cross sectional area of the side path is smaller than that of the micro flow channel.

(2) The microchip of (1), wherein liquid sent to the intermediate reservoir is sent through the micro flow channel leading to the intermediate reservoir together with air bubbles or a gas.

(3) The microchip of (1) or (2), wherein liquid sent to the intermediate reservoir contains at least 2 different types of liquids and is sent through the micro flow channel to the intermediate reservoir in a non-contact state in which a gas is present between the liquids.

(4) The microchip, described in any one of (1)-(3), wherein of liquids sent to the intermediate reservoir, the total amount of the liquids containing no liquid of the most upstream side is smaller than the capacity Vs.

(5) The microchip, described in any one of (1)-(4), wherein the inner wall surface of the side path is hydrophobic.

(6) In a liquid sending method for a microchip having a micro flow channel and an intermediate reservoir, with a capacity Vs smaller than total amount of liquid to be sent and a side path, to temporally store liquid having been sent through the micro flow channel in a flow channel of the micro flow channel wherein the side path communicatively connects a micro flow channel on an upstream side of the intermediate reservoir to a micro flow channel on a downstream side of the intermediate reservoir and a cross sectional area of the side path is smaller than that of the micro flow channel, the liquid sending method for a microchip comprising an initial step to arrange at least 2 liquid clusters in the micro flow channel of the upstream side; a storing step to store the liquids, having been arranged in the micro flow channel by applying a liquid sending pressure to the downstream side, by liquid sending to the intermediate reservoir; a filling step to fill the downstream side end portion of the side path with the sent liquids by sending all the liquids having been arranged in the micro flow channel to the intermediate reservoir; and a liquid sending step to send the liquids having been stored in the intermediate reservoir to the micro flow channel of the downstream side.

(7) In a liquid sending method for a microchip having a micro flow channel and an intermediate reservoir, with a capacity Vs smaller than total amount of liquid to be sent and a side path, to temporally store liquid having been sent through the micro flow channel in a flow channel of the micro flow channel wherein the side path communicatively connects a micro flow channel on the upstream side of the intermediate reservoir to a micro flow channel on the downstream side of the intermediate reservoir and a cross sectional area of the side path is smaller than that of the micro flow channel, the liquid sending method for a microchip comprising: an initial step to arrange at least 2 different types of liquids in the micro flow channel of the upstream side in a non-contact state in which a gas is present between the liquids; a storing step to store the liquids, having been arranged in the micro flow channel by applying a liquid sending pressure to the downstream side, by sequential liquid sending to the intermediate reservoir; a filling step to fill the downstream side end portion of the side path with the sent liquids by sending all the liquids having been arranged in the micro flow channel to the intermediate reservoir; and a liquid sending step to send the liquids having been stored in the intermediate reservoir to the micro flow channel of the downstream side.

(8) A liquid sending method for a microchip, described in (6) or (7), wherein of liquids sent to the intermediate reservoir, the total amount of the liquids containing no liquid of the most upstream side is smaller than the capacity Vs.

(9) The liquid sending method for a microchip, described in any one of claims (6) to (8), wherein a wall surface of the side path is hydrophobic.

Effects of the Invention

According to the present invention, there can be provided a microchip capable of sending liquid in a micro flow channel to a predetermined position and of carrying out liquid sending to a predetermined position by mixing at least 2 liquid clusters even with a simple flow channel constitution, independently of pressure difference.

Further, even in a state in which air bubbles or a gas coexists with liquid, such air bubbles or a gas is eliminated in an intermediate reservoir and then liquid sending to the downstream side can be carried out.

BRIEF DESCRIPTION OF THE DRAWINGS

FIG. 8 is a view illustrating the procedure to send a plurality of different liquids having been arranged in a micro flow channel r1 to the intermediate reservoir 139, in which

DESCRIPTION OF THE ALPHANUMERIC DESIGNATIONS

1: microchip
5: micropump
6: pump connection section
g: upstream opening section
i: injection hole
139: intermediate reservoir
139$m$: main section
139$s$: side path
e: downstream side end portion
CN: communication connection section
148: detection section
160: liquid waste section
70: drive liquid tank Preferred Embodiment of the Invention The present invention will now be described based on an embodiment that by no means limits the scope of the present invention.

[Device Constitution of an Analysis System]

Figure 1:
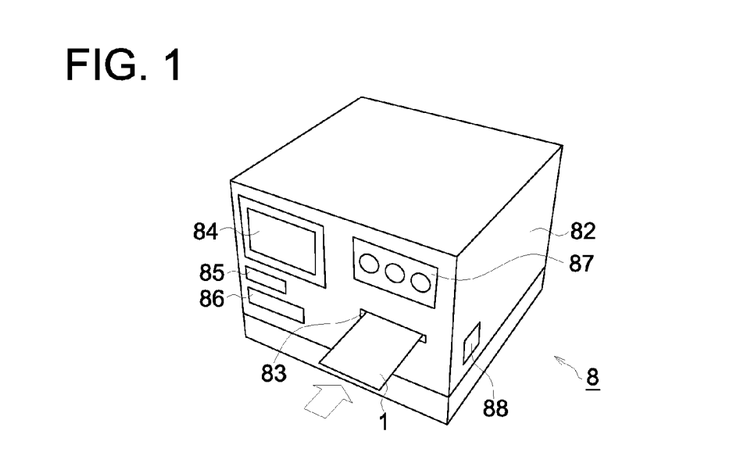
FIG. 1 is an external view of a microchip analysis system 8 employing a microchip according to the present embodiment.

FIG. 1 is an external view of a microchip analysis system 8 employing a microchip according to the present embodiment. The microchip analysis system 8 is a device to automatically allow a specimen and a reagent having been previously injected into the microchip 1 to react together and to automatically output the reaction result.

The housing 82 of the microchip analysis system 8 is provided with an insertion opening 83 to insert the microchip 1 into the device, a display section 84, a memory card slot 85, a print output opening 86, an operation panel 87, and an external input-output terminal 88.

The testing person inserts a microchip 1 in the arrow direction of FIG. 1 and operates the operation panel 87 to initiate a test. In the interior of the microchip analysis system 8, the test for reaction inside the microchip 1 is automatically carried out, and on the termination of the test, the result is displayed in the display section 84. The test result can be output as a print from the print output opening 86 or memorized in a memory card inserted in the memory card slot 85 by operating the operation panel 87. Further, data can be stored in a personal computer from the external input-output terminal 88, for example, using a LAN cable. After the termination of the test, the testing person ejects the microchip 1 from the insertion opening 83.

Figure 2:
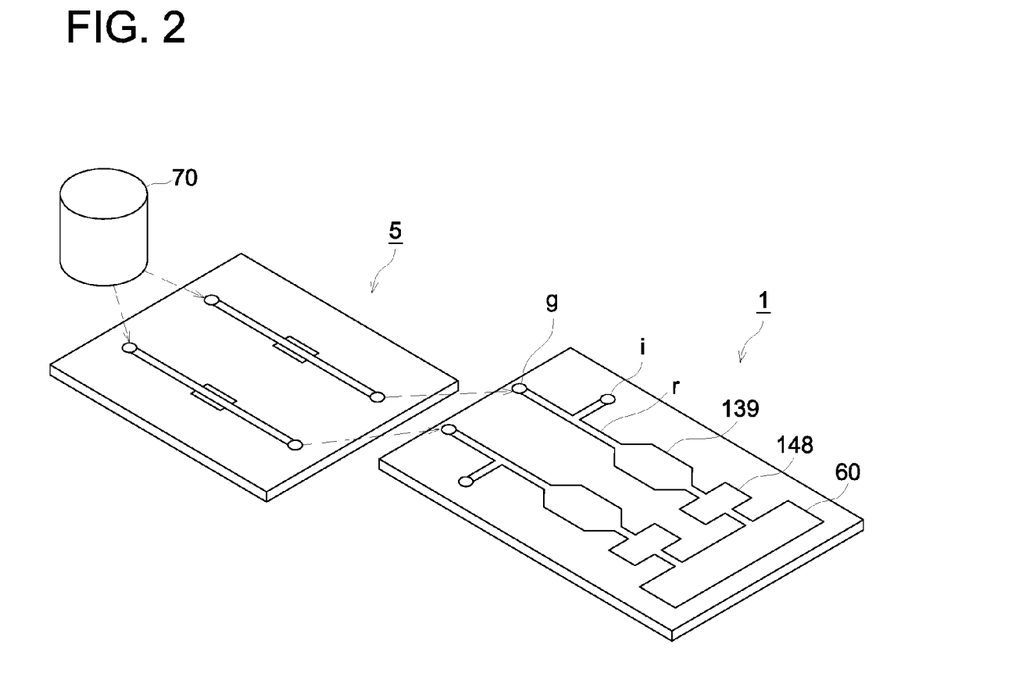
FIG. 2 is a schematic perspective view of a microchip analysis system 8 employing a microchip according to the present embodiment.
Figure 3:
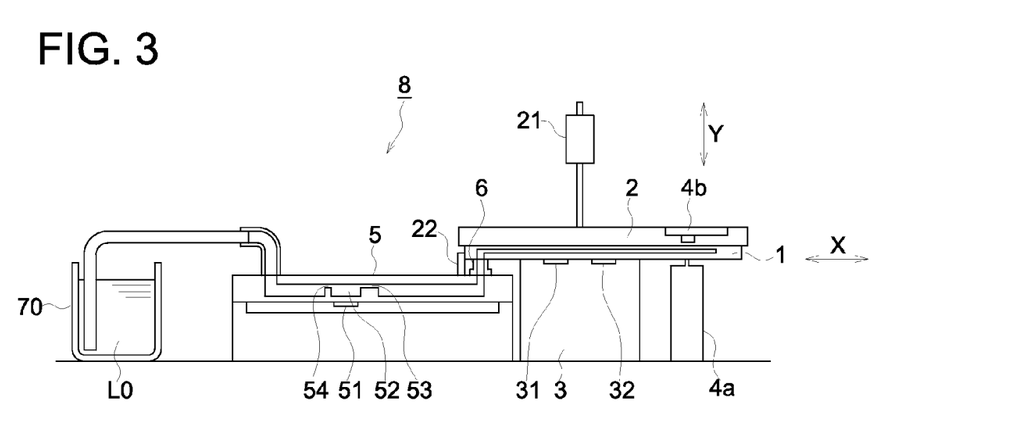
FIG. 3 is a constitutional view of a microchip analysis system 8 employing a microchip according to the present embodiment.

FIG. 2 is a schematic perspective view of the microchip analysis system 8 employing a microchip according to the present embodiment and FIG. 3 is a constitutional view thereof In FIG. 2 and FIG. 3, a state is shown in which a microchip has been inserted from the insertion opening 83 shown in FIG. 1 and then setting has been completed.

The microchip analysis system 8 is provided with a drive liquid tank 70 to store a drive liquid LO for sending a specimen and a reagent having been previously injected into a microchip 1; a micropump 5 to feed the drive liquid LO to the microchip 1; a pump connection section 6 to connect the micropump 5 to the microchip 1 so as for the drive liquid LO not to leak; a temperature adjustment unit 3 to carry out temperature adjustment for required portions of the microchip 1; a chip pressing plate 2 to bring the microchip 1 into close contact with the temperature adjustment unit 3 and the pump connection section 6 for displacement prevention; a pressing plate drive section 21 to move the chip pressing plate 2 up and down; a regulation member 22 to accurately position the microchip 1 to the micropump 5; and a light detection section 4 (4a and 4b) to detect the reaction state between the specimen and the reagent in the microchip 1.

The chip pressing plate 2 is withdrawn upward from the position shown in FIG. 3 in the initial state. Thereby, a microchip 1 can be inserted and ejected in the arrow X direction and the testing person inserts the microchip 1 from the insertion opening 83 (refer to FIG. 1) until brought into contact with the regulation member 22. Thereafter, the chip pressing plate 2 is moved down by the pressing plate drive section 21 and brought into contact with the microchip 1. The bottom surface of the microchip 1 is brought into close contact with the temperature adjustment unit 3 and the pump connection section 6.

The temperature adjustment unit 3 is provided with a Peltier element 31 and a heater 32 on the plane facing the microchip 1. When the microchip 1 is set in the microchip analysis system 8, the Peltier element 31 and the heater 32 are allowed to make close contact with the microchip 1. The portion storing a reagent is cooled by the Peltier element 31 so as for the reagent not to be denatured and also the intermediate reservoir 139 to join the specimen with the reagent for reaction is heated by the heater 32 for reaction acceleration.

In the light detection section 4 incorporating a light emission section 4a and a light receiving section 4b, light from the light emission section 4a incorporating, for example, a mercury lamp is irradiated to the microchip 1 as excitation light via an excitation filter to allow light having a wavelength in a specific range to pass, and then fluorescence emitted from a fluorescent substance present in the detection section 148 of the microchip 1 is allowed to be transmitted, whereby the transmitted light is detected by the light receiving section 4b. The light receiving section 4b is integrally arranged in the chip pressing plate 2. The light emission section 4a and the light receiving section 4b are arranged opposite to the detection section 148 of the microchip 1 shown in FIG. 3.

An example of a micropump employing a piezoelectric element will now be described with no limitation, and therefore any appropriate syringe pump, diaphragm-type micropump, or electro-osmotic flow pump may be used.

The micropump 5 incorporates a pump chamber 52, a piezoelectric element 51 to vary the capacity of the pump chamber 52, a first narrowed flow channel 53 positioned on the microchip 1 side of the pump chamber 52, and a second narrowed flow channel 54 positioned on the drive liquid tank 70 side of the pump chamber. The first narrowed flow channel 53 and the second narrowed flow channel 54 each have a reduced narrow flow channel. The first narrowed flow channel 53 has a longer flow channel than the second narrowed flow channel 54.

When a drive liquid LO is sent in the forward direction (in the direction forward the microchip 1), initially, the piezoelectric element 51 is driven to rapidly decrease the capacity of the pump chamber 52. Then, in the second narrowed flow channel 54 which is the shorter narrowed flow channel, turbulence is generated, and then the flow channel resistance of the second narrowed flow channel 54 becomes relatively larger than that of the first narrowed flow channel 53 which is the longer narrowed flow channel. Thereby, the drive liquid LO in the pump chamber 52 is dominantly pushed out and sent toward the first narrowed flow channel 53. Subsequently, the piezoelectric element 51 is driven to gradually increase the capacity of the pump chamber 52. Then, as the capacity of the pump chamber 52 increases, the drive liquid LO flows in from the first narrowed flow channel 53 and the second narrowed flow channel 54. At this moment, since the second narrowed flow channel 54 is shorter than the first narrowed flow channel 53, the second narrowed flow channel 54 is smaller in flow channel resistance than the first narrowed flow channel 53, whereby the drive liquid LO dominantly flows into the pump chamber 52 from the second narrowed flow channel 54. The above movements are repeated by the piezoelectric element 51 to send the drive liquid LO in the forward direction.

In contrast, when the drive liquid LO is sent in the reverse direction (in the direction toward the drive liquid tank 70), initially, the piezoelectric element 51 is driven to gradually decrease the capacity of the pump chamber 52. Then, since the second narrowed flow channel 54 is shorter than the first narrowed flow channel 53, the second narrowed flow channel 54 becomes smaller in flow channel resistance than the first narrowed flow channel 53. Thereby, the drive liquid LO in the pump chamber 52 is dominantly pushed out and sent toward the second narrowed flow channel 54. Subsequently, the piezoelectric element 51 is driven to rapidly increase the capacity of the pump chamber 52. Then, as the capacity of the pump chamber 52 increases, the drive liquid LO flows in from the first narrowed flow channel 53 and the second narrowed flow channel 54. At this moment, turbulence is generated in the second narrowed flow channel 54 which is the shorter narrowed flow channel, and then the flow channel resistance in the second narrowed flow channel 54 becomes relatively larger than that of first narrowed flow channel 53 which is the longer narrowed flow channel. Thereby, the drive liquid LO dominantly flows into the pump chamber 52 from the first narrowed flow channel 53. The above movements are repeated by the piezoelectric element 51, whereby the drive liquid LO is sent in the reverse direction. Further, when the drive voltage applied to the piezoelectric element 51 is changed, the liquid sending pressure of the drive liquid LO can be changed.

The contact surface of the pump connection section 6 is preferably formed with a resin with flexibility (elasticity or shape conformity) such as polytetrafluoroethylene or a silicone resin to ensure required sealing properties and to prevent drive liquid leakage. The contact surface having such flexibility may be formed with a constitutional substrate itself of a microchip or may be formed with another member with flexibility bonded to the periphery of the flow channel opening of the pump connection section 6.

[Constitution of Microchip 1]

Figure 4:
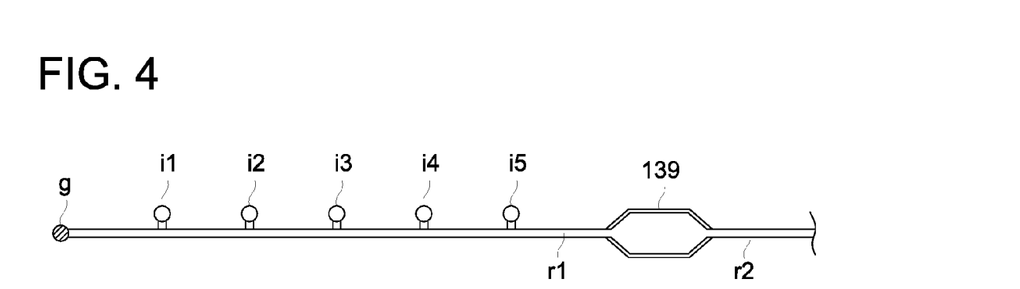
FIG. 4 shows one example of a microchip 1 according to the present embodiment.

FIG. 4 shows one example of a microchip 1 according to the present embodiment. In the figure, an arrangement of main sections of the micro flow channel r and the intermediate reservoir 139 is schematically shown in the state where a sheet-shaped cover substrate is removed.

In the microchip 1, arranged are a micro flow channel r and flow channel elements to carry out mixing and reaction of a liquid reagent and similarly a liquid specimen (sample) on the microchip 1 using a water-repellent (also referred to as "hydrophobic") substrate. As materials for such a substrate, exemplified are resins such as polystyrene, polyethylene, polypropylene, polyethylene terephthalate, polyethylene naphthalate, polyethylene vinyl alcohol, polycarbonate, polymethylpentene, fluorocarbon, and saturated cyclic polyolefins. Of these, polystyrene is easily microfabricated due to excellent transparency, mechanical characteristics, and molding properties, resulting in a preferable forming material for a groove formed substrate. Further, a similar water-repellent substrate is used for an unshown sheet-shaped cover substrate.

The micro flow channel r is formed in the order of micrometers, for example, having a width w of several tens—several hundreds μm, preferably 50-300 μm and a height h of about 25-1000 μm, preferably 50-300 μm.

The designation g is an upstream opening section opened to the exterior from one face of the microchip 1. When the microchip 1 is overlapping-connected to the micropump 5 via the pump connection section 6, the upstream opening section g is positioned to a flow channel opening provided in the connection face of the micropump 5 to be communication-connected to the micropump 5. Then, the drive liquid LO to be sent from the upstream opening section g is injected. Herein, a plurality of such upstream opening sections g may be provided.

And, the designation i (i1-i5) represents a set of injection holes to inject liquid such as a specimen or a reagent (hereinafter also referred to simply as liquid), being a set of openings opened to the exterior from the upper face of the microchip 1. Such liquid is injected into each injection hole (i1-i5) in the state where the upstream opening section g is opened. The thus-injected liquid is sent through a micro flow channel toward the upstream opening section g in the vicinity. In the present embodiment shown in the figure, liquid is sequentially injected into the holes ranging from the injection hole i5 of the downstream side to the injection hole i1 of the upstream side. The injected liquid is stored in the micro flow channel r1 of the upstream side more than in the intermediate reservoir 139. During liquid injection, the upstream opening section g and the injection holes i1-i5 are open, and then after reagent injection, only the injection holes i1-i5 are sealed. Then, a liquid sending pressure is applied to the liquid such as a reagent or a specimen, in the presence of gas such as air or an inert gas therebetween, by the drive liquid LO sent in from the micropump 5 communication-connected to the upstream opening section g, whereby the liquid is sent in the micro flow channel r.

Figure 5A:
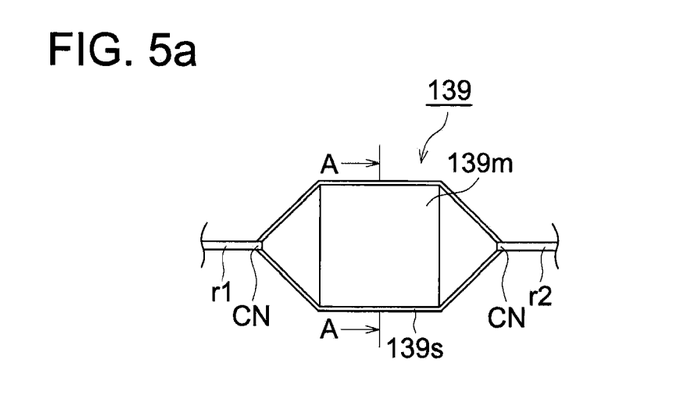
FIG. 5A, in FIG. 5, is a top view of the periphery of an intermediate reservoir 139.
Figure 5B:
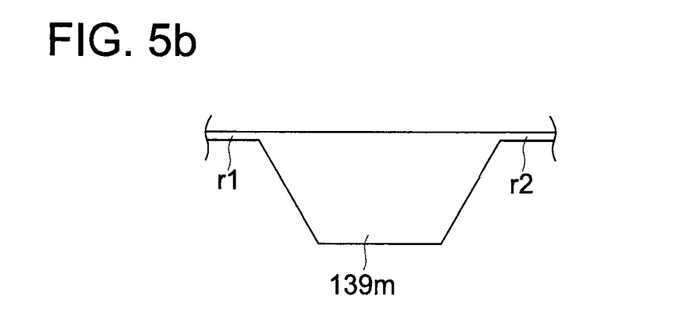
FIG. 5B is a sectional view of the periphery of the intermediate reservoir 139.
Figure 5C:
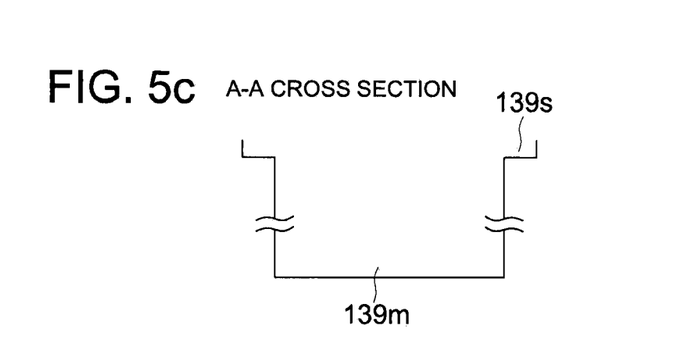
FIG. 5C is an A-A sectional view in FIG. 5A.
Figure 6A:
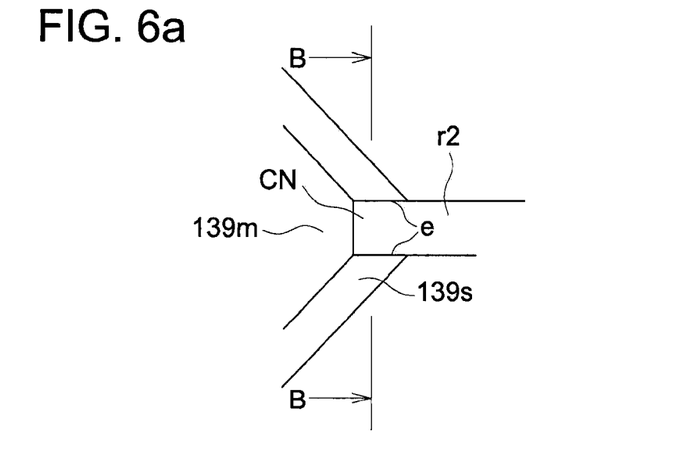
FIG. 6A, in FIG. 6, is a top view of the downstream side outlet periphery of the intermediate reservoir 139
Figure 6B:
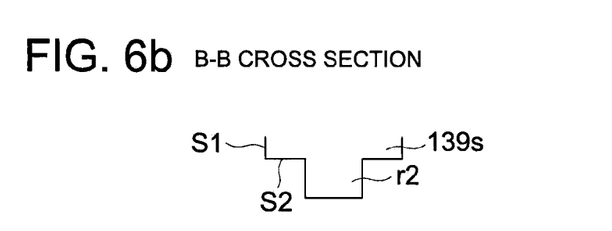
FIG. 6B is a B-B sectional view in FIG. 6A.
Figure 7:
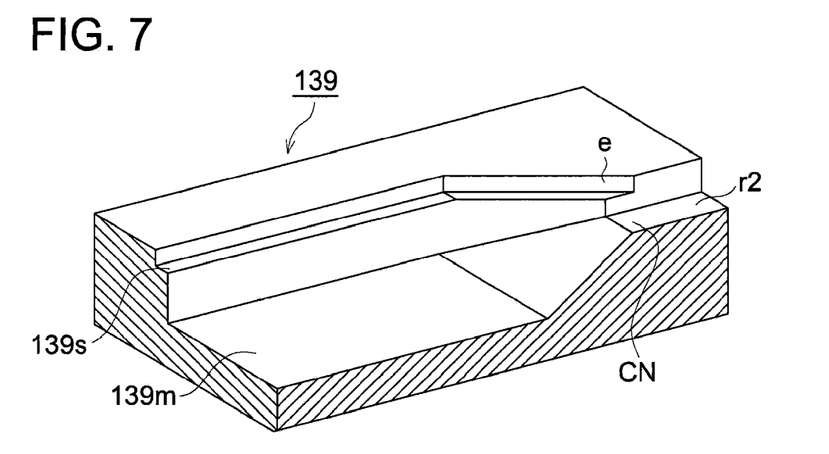
FIG. 7 is a perspective view of the center cross-section of the periphery of the intermediate reservoir 139.

With reference to FIG. 5-FIG. 7, the constitution of the intermediate reservoir 139 will now be described. FIG. 5 is an enlarged view of the periphery of the intermediate reservoir 139 of the microchip shown in FIG. 4. FIG. 5A is a top view thereof, FIG. 5B is a sectional view thereof, and FIG. 5C is an A-A sectional view thereof. FIG. 6 is an enlarged view of the downstream side outlet periphery of the intermediate reservoir 139. FIG. 6A is a top view thereof and FIG. 6B is a B-B sectional view thereof. FIG. 7 is a perspective view of the center cross-section of the intermediate reservoir 139.

As shown in FIG. 5-FIG. 7, the intermediate reservoir 139 incorporates a main section 139$m$ and a side path 139$s$. The side path 139$s$ is communication-connected to a micro flow channel r1 of the upstream side and a micro flow channel r2 of the downstream side at communication connection sections CN. In the example shown in the figures, a side path 139$s$ is provided each on both sides of the main section 139$m$ of the intermediate reservoir 139, but not only in this case, such a side path 139$s$ may be provided only on one side.

In the embodiment shown in the figures, the top surface positions of the side path 139$s$ and the micro flow channel r are the same but the heights (depths) and the widths thereof differ. The side path 139$s$ is a rectangular shape having a width of 250 82 m and a height (depth) of 100 μm and the cross sectional area thereof is $25 \times 10^{-9}$ m$^2$. The micro flow channels r1 and r2 are rectangular shapes each having a width of 300 μm and a height of 250 μm and the cross sectional area thereof is $75 \times 10^{-9}$ m$^2$. Namely, the side path 139$s$ is formed so that the cross sectional area thereof is smaller than that of the micro flow channel r1 of the upstream side. Herein, the cross sectional area of the side path 139$s$ may be decreased to a width of 250 μm and a height of 50 μm.

Further, a cover substrate allowed to adhere to the top surface unshown and the surfaces of the inner wall surfaces s1 and s2 of the side path 139$s$ each are formed with water-repellent materials. In this manner, the side path 139$s$ is allowed to have a smaller cross sectional area than the micro flow channel r1 of the upstream side and is formed with a water-repellent material, whereby the flow channel resistance of the side path 139$s$ is extremely larger than that of the micro flow channel r1. Namely, liquid is difficult to pass but gas can easily pass through the side path 139$s$.

[Capacity of Intermediate Reservoir 139]

The entire length of the intermediate reservoir 139 is 4000 μm. The width of the main section 139$m$ is 1500 μm in a flat bottom surface portion having the largest cross sectional area (refer to FIG. 5C) and the height thereof is 1500 μm. The width and height thereof are larger than those of the micro flow channel r. Further, the length of the flat portion is 2000 μm. Herein, the intermediate reservoir 139 may be formed in such a manner that the height of the main section 139$m$ thereof is allowed to be 250 μm which is the same height as the micro flow channel r1 and only the width direction is allowed to be larger. In this manner, a microchip can be allowed to have a simpler shape.

Further, the total amount of liquid sent to the intermediate reservoir 139 is larger than the capacity Vs thereof. Namely, the capacity Vs is allowed to be smaller than the total amount of the liquid. The reason for such setting will be described later. Herein, in the present invention, the intermediate reservoir refers to a region sandwiched by the upstream side end portion and the downstream side end portion of the side path. Liquid having been provided from the upstream side is temporally stored in this region.

[Liquid Sending Method]

FIG. 8 is a view illustrating the procedure to send a plurality of different liquids having been arranged in the micro flow channel r1 to the intermediate reservoir 139.

Figure 8A:
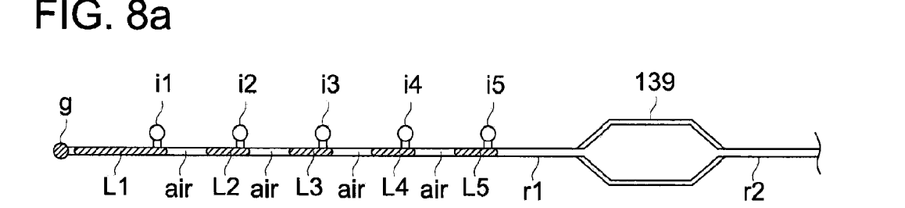
FIG. 8A, FIG. 8B, FIG. 8C, and FIG. 8D are views illustrating an initial step, a storing step, a filling step, and a liquid sending step, respectively.

FIG. 8A is a view showing "an initial step," being a view showing a state where different types of liquids L1-L5 each or liquids L1-L5 each being a liquid cluster of the same type are injected from injection holes i1-i5. As described above, the injection holes i1-i5 are sealed after liquid injection. Air is present between the liquids L1-L5 each, whereby a non-contact state is maintained between adjacent liquids. Thereby, no liquids each are mixed in the initial arrangement shown in the figure. Further, the total liquid amount of the liquids L1-L5 is allowed to be larger than the capacity Vs of the intermediate reservoir 139.

[Liquid Volume]

"The total liquid amount sent to the intermediate reservoir" will now be described. The total liquid amount referred to herein refers to the amount of liquids sent to the intermediate reservoir 139 and of the liquids having been injected from the injection holes i1-i5 each, those stored in the micro flow channel r1 are referred to. Namely, the total amount of the liquids L1-L5 is referred to. The arranged amount of the liquid L1 is 3 μl in the micro flow channel r1. Similarly, the amount of each of the liquids L2-L5 is 1.5 μl. Therefore, the total amount of the liquids (L2-L5) without the liquid L1 of the most upstream side is 6 μl. And, the total amount including all the liquids is allowed to be 9 μl. Thereby, the volume of the former is smaller than the capacity Vs of the intermediate reservoir 139 which is 7.3 μl, and then by adding the liquid L1 amount of the upstream side to this amount, the total amount of the liquid L after addition becomes larger than the capacity Vs of the intermediate reservoir 139. Namely, the total amount L (L1-L5) of all the liquids sent to the intermediate reservoir 139 is larger than the capacity Vs of the intermediate reservoir, and the total amount (L2-L5) of the liquids without the liquid L1 of the most upstream side is smaller than the capacity Vs.

Figure 8B:
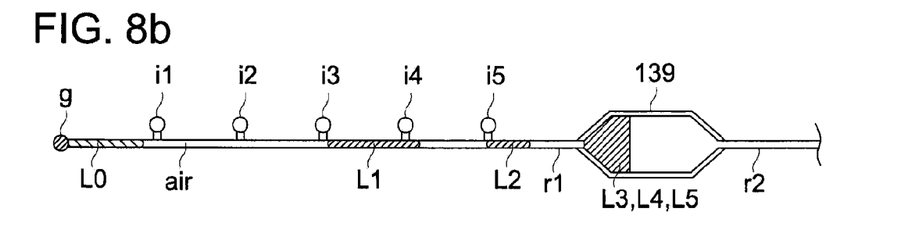

FIG. 8B is a view illustrating "a storing step" to send liquid to the intermediate reservoir 139. A drive liquid LO is injected from the upstream side opening section g using the micropump 5 for liquid sending. The liquids L1-L5 having been arranged in the micro flow channel r1 in the presence of air therebetween via the liquid sending pressure of the drive liquid LO are sent to the intermediate reservoir 139. At the moment when the front end of each sent liquid enters the intermediate reservoir 139, the communication connection section CN of the side path 139s and the micro flow channel r1 (or the upstream side end portion of the side path 139s) is sealed by the liquid, whereby air present at the back the liquid cannot be passed through the side path 139s. When the end portion of the sent liquid is passed through the communication connection section CN of the side path 139s and the micro flow channel r1, the communication connection section CN is opened. Thereby, the air present at the back of the liquid passes the liquid and then the air escapes toward the micro flow channel r2 of the downstream side. Namely, in the state where the air present between the liquids L1-L5 is eliminated, the liquids L1-L5 each can be joined together in the intermediate reservoir 139. Further, with such a constitution, even when liquid sending pressure by air is increased, the liquids L1-L5 can be allowed to stop in the intermediate reservoir 139, independently of the liquid sending pressure.

In the state shown in FIG. 8B, the liquids L3, L4, and L5, having been arranged on the intermediate reservoir 139 side (the downstream side) of the micro flow channel r1 in the initial arrangement, are mixed together in the intermediate reservoir 139 (the main section 139m). Herein, as described above, the intermediate reservoir 139 refers to a region sandwiched by the upstream side end portion and the downstream side end portion e of the side path 139s. As shown in the figure, in the interior of the intermediate reservoir 139, when the upstream side end portion of the side path 139s is a boundary which is then designated as the base point, liquid having been sent toward the downstream side beyond the base point is gradually accumulated.

Figure 8C:
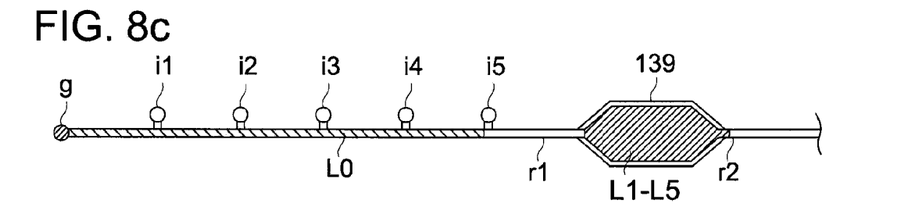

FIG. 8C is a view illustrating "a filling step." In the figure, a state is created in which all the liquid L (L1-L5) has been sent to the intermediate reservoir 139 and mixed together. As described above, setting is carried out in such a manner that "the total amount of all the liquid L (L1-L5) is larger than the capacity Vs of the intermediate reservoir 139," whereby the communication connection sections CN of the upstream side and the downstream side of the intermediate reservoir 139 each are filled with the sent liquid L (L1-L5). Especially, the downstream side end portion e of the micro flow channel 139s is sealed by the sent liquid L. In such a state, it is impossible that air passes through the side path 139s from the micro flow channel r1 and then escapes from the downstream side end portion e of the side path 139s to the micro flow channel r2. Thereby, the air cannot pass the liquid L (L1-L5) in the intermediate reservoir 139. Namely, the liquid sending pressure by the drive liquid LO via the air is again allowed to be applied to the liquid L (L1-L5).

Figure 8D:
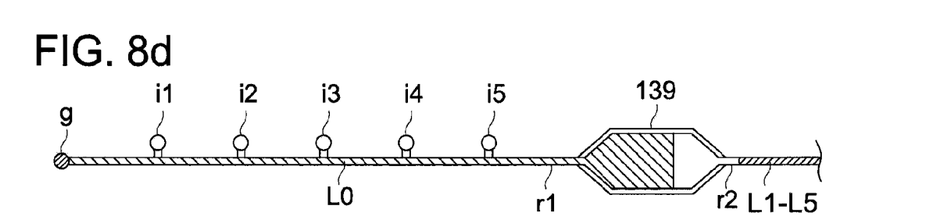

FIG. 8D is a view illustrating "a liquid sending step." In the figure, liquid sending pressure is applied to the liquid L (L1-L5) via air by the drive liquid LO by driving the micropump again for liquid sending to the detection section 148 of the downstream side. The reaction of the pushed-out liquid L (L1-L5) is optically detected in the detection section 148 and then the test process is terminated.

Herein, in the example shown in FIG. 8, one example has been described, with no limitation, in which an arrangement was made by allowing air to be present between the liquids L1-L5 of the same type. "A case in which air bubbles or air unintentionally coexists" with a liquid cluster may be included. Also in such a case, the liquid is sent to the intermediate reservoir 139 together with air or air bubbles, whereby in the intermediate reservoir 139, the air or air bubbles having unintentionally coexisted with the liquid can be eliminated. Herein, in this case, at the moment when the amount of the provided liquid sent as a cluster to the intermediate reservoir 139 becomes larger than the capacity Vs of the intermediate reservoir 139, the liquid is sent to the downstream side. Incidentally, "the case in which air bubbles or air coexists unintentionally" refers to, for example, a case in which liquid temperature is increased or pressure is decreased, whereby air such as oxygen dissolved in the liquid is released to give air bubbles; or a case in which when liquid is injected into the micro flow channel, air coexistence results.

According to the present embodiment, there can be provided a microchip capable of sending liquid in a micro flow channel to a predetermined position and of carrying out liquid sending to a predetermined position by mixing at least 2 liquid clusters even with a simple flow channel constitution, independently of pressure difference. Further, a drive liquid LO and a liquid L (L1-L5) can be sent via air in a non-contact manner, whereby the drive liquid LO can be selected with no consideration of adverse effects to a test.

The invention claimed is:

1. A liquid sending method for a microchip having a micro flow channel and an intermediate reservoir, with a capacity Vs smaller than total amount of liquid to be sent and a side path, to temporally store liquid having been sent through the micro flow channel in a flow channel of the micro flow channel wherein the side path communicatively connects a micro flow channel on an upstream side of the intermediate reservoir to a micro flow channel on a downstream side of the intermediate reservoir and a cross sectional area of the side path is smaller than that of the micro flow channel, the liquid sending method for a microchip comprising:

arranging at least 2 liquid clusters in the micro flow channel of the upstream side in a non-contact state in which gas is present between adjacent liquid clusters;

storing the liquid clusters, having been arranged in the micro flow channel by applying a liquid sending pressure to the downstream side, by liquid sending to the intermediate reservoir;

filling the downstream side end portion of the side path with the sent liquids by sending all the liquid of the liquid clusters having been arranged in the micro flow channel to the intermediate reservoir; and sending the liquids having been stored in the intermediate reservoir to the micro flow channel of the downstream side.

2. A liquid sending method for a microchip having a micro flow channel and an intermediate reservoir, with a capacity Vs smaller than total amount of liquid to be sent and a side path, to temporally store liquid having been sent through the micro flow channel in a flow channel of the micro flow channel wherein the side path communicatively connects a micro flow channel on the upstream side of the intermediate reservoir to a micro flow channel on the downstream side of the intermediate reservoir and a cross sectional area of the side path is smaller than that of the micro flow channel, the liquid sending method for a microchip comprising:

arranging at least 2 liquid clusters of different types of liquids in the micro flow channel of the upstream side in a non-contact state in which a gas is present between the liquids;

storing the liquid clusters, having been arranged in the micro flow channel by applying a liquid sending pressure to the downstream side, by sequential liquid sending to the intermediate reservoir;

filling the downstream side end portion of the side path with the sent liquids by sending all the liquid of the liquid clusters having been arranged in the micro flow channel to the intermediate reservoir; and a liquid sending step to send the liquids having been stored in the intermediate reservoir to the micro flow channel of the downstream side.

3. The liquid sending method for a microchip, described in claim 1, wherein of liquids sent to the intermediate reservoir, the total amount of the liquids containing no liquid of the most upstream side is smaller than the capacity Vs.

4. The liquid sending method for a microchip, described in claim 2, wherein of liquids sent to the intermediate reservoir, the total amount of the liquids containing no liquid of the most upstream side is smaller than the capacity Vs.

5. The liquid sending method for a microchip, described in claim 1, wherein a wall surface of the side path is hydrophobic.

6. The liquid sending method for a microchip, described in claim 2, wherein a wall surface of the side path is hydrophobic.

7. The liquid sending method for a microchip, described in claim 3, wherein a wall surface of the side path is hydrophobic.

8. The liquid sending method for a microchip, described in claim 4, wherein a wall surface of the side path is hydrophobic.

* * * * *